(12) United States Patent
Salcudean et al.

(10) Patent No.: US 6,368,332 B1
(45) Date of Patent: Apr. 9, 2002

(54) MOTION TRACKING PLATFORM FOR RELATIVE MOTION CANCELLATION FOR SURGERY

(76) Inventors: Septimiu Edmund Salcudean, 4338 West 2nd Avenue, Vancouver, B.C. (CA), V6R 1K3; Samuel Victor Lichtenstein, 6410 Cedarhurst Street, Vancouver, B.C. (CA), V2N 4J1; Ana Luisa Trejos, B-603 St. Claire Avenue West, Toronto, ON (CA), M6C 1A3; Farrokh Sassani, 3990 Lynn Valley Road, North Vancouver, B.C. (CA), V7K 2S9; Terence J. Gilhuly, 1550 Vine St Apt. 208, Vancouver, B.C. (CA), V6K 3J2

( * ) Notice: Subject to any disclaimer, the term of this patent is extended or adjusted under 35 U.S.C. 154(b) by 0 days.

(21) Appl. No.: 09/521,014

(22) Filed: Mar. 7, 2000

Related U.S. Application Data

(60) Provisional application No. 60/123,394, filed on Mar. 8, 1999.

(51) Int. Cl.[7] .............................................. A61B 19/00
(52) U.S. Cl. ........................... 606/130; 606/1; 128/897; 600/102
(58) Field of Search ..................... 606/130, 1; 128/898, 128/897; 600/424, 429, 101, 102, 595; 901/1, 9, 8, 41, 48; 395/86; 414/1

(56) References Cited

U.S. PATENT DOCUMENTS

| | | | | |
|---|---|---|---|---|
| 5,598,269 A | * | 1/1997 | Kitaevich et al. ........... | 606/130 |
| 5,762,458 A | * | 6/1998 | Wang et al. ................. | 606/130 |
| 5,871,017 A | * | 2/1999 | Mayer ......................... | 128/897 |
| 5,967,980 A | * | 10/1999 | Ferre et al. .................. | 600/424 |
| 5,971,976 A | * | 10/1999 | Wang et al. .................... | 606/1 |
| 6,001,108 A | * | 12/1999 | Wang et al. ................. | 606/130 |
| 6,006,127 A | * | 12/1999 | Van Der Brug et al. .... | 600/429 |

* cited by examiner

Primary Examiner—Pedro Philogene
(74) Attorney, Agent, or Firm—C. A. Rowley

(57) ABSTRACT

A system for performing coronary artery bypass grafting surgery on the beating heart senses the movement of the surgical area of the heart to be worked on and moves a support with a controlled motion follows the motion of the surgical area on the heart surface in real time. To provide a steady image of the workspace a vision system can be attached to the support. This approach can be used for open-heart surgery as well as other less invasive procedures like minimally invasive direct coronary artery bypass (MIDCAB) or thoracoscopic surgery.

19 Claims, 13 Drawing Sheets

MOTION TRACKING PLATFORM FOR RELATIVE MOTION CANCELLATION FOR SURGERY

This Appln claims benefit of Prov. No. 60/123,394 filed Mar. 8, 1999.

FIELD OF THE INVENTION

The present invention describes a method for performing surgery on the beating heart by coordinating movement of a moving support for the hands of the surgeon and/or the surgeon's tools in synchrony with the sensed movement of a surgical area on the heart surface

BACKGROUND TO THE PRESENT INVENTION

The coronary arteries are very narrow blood vessels (less than 3 mm in diameter) that transport nutrient-rich blood to the heart muscle. Coronary artery disease is caused by the accumulation of materials on their inner walls, causing them to further narrow and reducing the blood flow to some parts of the heart muscle. A complete obstruction causes the tissue to die and the heart to go into cardiac arrest.

There are three main methods for treatment of narrowed coronary arteries. The only method that does not involve surgery is drug therapy, which can improve blood flow and reduce accumulation of materials on the coronary walls. A first interventional method, called angioplasty, employs a catheter that is placed inside the narrowed artery to widen the blood vessel. A second and most drastic interventional method is called coronary artery bypass grafting surgery (CABG).

CABG surgery is a major surgical procedure that involves general anesthesia. Of all coronary artery disease treatments it is the most effective for relief of angina and has been proven to prolong patient survival. The goal of the operation is to provide a new channel for the blood to reach the dying tissue. This new channel is a blood vessel taken from the patient's own body, generally a piece of vein from the leg or the arm, or an artery from the chest wall. One end of this vessel is grafted to the aorta and the other end is grafted to the coronary artery downstream from the obstruction. When the blood vessel used is an artery from the chest wall, it is grafted directly to the coronary artery. In most cases the patient is put on cardiopulmonary bypass, which allows the heart to be stopped while the circulation and the heart and lung machine performs filtration of the blood. However, there are several damaging effects that arise due to the use of the heart and lung machine. These include: anemia, red blood cell aggregation, gaseous and particulate emboli, hemolysis (red blood cell damage), localized ischemia, among others. The need for stopping the heart arises from the need to obtain a stable suturing area because the suturing process is a complex procedure that involves high skill and accuracy.

Coronary arteries are located on the surface of the heart, therefore during CABG surgery there is no need to open any of the heart chambers. One technical requirement to perform CABG is to have a bloodless anastomotic field, which in the case of surgery on the beating heart can be achieved by a temporary coronary occlusion. Since the only reason for stopping the heart is for stabilization purposes, if there is a way of performing the grafts while the heart is in motion, the heart can itself perform the circulation and filtration of the blood. This eliminates the damaging effects of the cardiopulmonary bypass.

Several approaches have been proposed to perform CABG surgery on the beating heart. All of them consist of stabilizing the heart tissue that surrounds the surgical site without causing significant damage. Systems have been developed that consist of a horseshoe shaped apparatus that presses down on the heart surface to immobilize the area around the coronary artery where the suturing is to take place (see Guidant Access MV stabilizer Set, Guidant Corporation, http://www.guidant.com/products/surgery/access.htm and Gu Y J, Mariani M A, van Oeveren W, Grandjean J G, Boonstra P W. "Reduction of the inflammatory response in patients undergoing minimally invasive coronary artery bypass grafting", Annals of Thoracic Surgery 1998; 65:420–4). Since these devices work by pressure, the force that they exert has to be large enough so that the apparatus is in contact with the surface even when the heart is fully contracted. This presents the disadvantage of exerting stresses on the heart that can damage the tissue. Another disadvantage of such devices is that they can only be used to suture on the top surface of the heart. Furthermore, there is a considerable amount of time required to adjust the position of the stabilizing device on the surface of the heart.

Other approaches developed consist of using suction instead of pressure to stabilize the tissue. The disadvantage of such methods is that the stresses that are exerted on the tissue may be high even when used for short periods of time (Cornelius Borst, "Coronary Artery Bypass Grafting without Cardiopulmonary Bypass and without interruption of Native Coronary Flow using a novel Anastomosis Site Restraining Device ("Octopus"), "Journal of American College of Cardiology, vol. 27, no.6, pp. 1356–64, May, 1996.), and T. Gilhuly, S. E. Salcudean, K. Ashe, S. Lichtenstein and P. D. Lawrence, "Heart Stabilizer and Surgical Arm Design for Cardiac Surgery", 6 pages, 1998 IEEE International Conference on Robotics and Automation, Leuven, Belgium, May 1998).

Other recently developed systems (see, for example, the Zeus system developed by Computer Motion Inc. or the DaVinci system developed by Intuitive Surgical Inc.) use several interactive robotic arms to position the endoscope and to manipulate the surgical instruments. The surgeon views the surgical site while seated at an ergonomically enhanced console, from where he or she controls the motion of the instruments and the position of the endoscope. Such systems could, in principle, be modified so that the surgeon controls the motion of the robotic arms relative to a selected surgical site, with the robotic arms automatically tracking the motion of the surgical site. For this approach to be effective, the robotic arms have to be able to move fast enough to accurately track the motion of the surgical site. Therefore, two or three arms, each with 4–6 degrees of freedom, would have to move fast enough and accurately enough to track the surgical site. This poses numerous technical challenges. Therefore, the use of robots might still require that the heart be stopped by means of cardiopulmonary bypass.

U.S. Pat. No. 5,871,017 by Mayer discloses a moving hand support that is moved in synchrony with the heart to significantly reduce the relative motion between the heart and the coronary anastomosis site. This system employs a pacer that controls the beating of the heart and also controls the platform movement. The motion of the platform is produced by a cam, shaped so that the pattern of the oscillation follows the heart motion. In the system described in this patent the relative displacement between the moving platform (and, implicitly, the surgeon's instruments) and the surgical site can be significant, even if the heart motion is synchronized to the hand support by means of a pacer. In fact, it is likely that if the relative motion between the surgical site on the heart and the moving platform is significant, the teachings of this invention cannot be used effectively. Furthermore, cam mechanisms are suggested in U.S. Pat. No. 5,871,017 in order to track the motion of the heart. In fact, whether paced or not, the motion of the coronaries on the heart has been documented to be three dimensional and highly variable, and thus cannot be approximated well by a cam motion.

BRIEF DESCRIPTION OF THE INVENTION

It is an object of the present invention to provide a method and apparatus that enables virtual stabilization of the heart tissue without damaging forces exerted on it to allow coronary artery bypass grafting surgery to be performed without the use of the cardiopulmonary bypass and without damaging the heart tissue.

Broadly the present invention relates to a method for performing surgery comprising sensing the movement of a selected point and controlling the motion of a set point fixed in position relative to a platform that supports the surgeon's hands and instruments in accordance with said sensed movement so as to maintain a set displacement between said selected and said set points substantially constant.

Broadly the present invention also relates to an apparatus for assisting a surgeon in performing surgery comprising a sensor for sensing the movement of a selected point at or adjacent to a surgical site, a computer, means for providing said sensed movement to said computer, a surgical platform, means of moveably mounting said platform, a set point fixed in position relative to said platform, said computer controlling the movement of said set point fixed relative to said platform in said at least three degrees of movement in accordance with said sensed movement of said selected point to maintain a set displacement between said selected point and said set point substantially constant.

Preferably, said set displacement between said selected point and said set point is selectively defined.

Preferably said method comprises selecting said set point, selecting said selected point, selecting said set displacement and then commencing said controlling the movement of said set point on a platform.

Preferably, said surgical site is on a heart and said controlling comprises determining rhythm and trajectory of point s based on previously sensed historical movement of point s and controlling movement of point p based on said historical movement of point s and correcting said movement of point p based on current sensed movement of point s.

Preferably, said selectively defining comprises a voice control.

Preferably, said selectively defining comprises a joystick control.

Preferably, said selectively defining comprises a foot pedal control.

Preferably a camera system is mounted on and moves with said platform to provide a stabilized view of said surgical site.

BRIEF DESCRIPTION OF THE DRAWINGS

Further features, objects and advantages will be evident form the following detained description of the present invention taken in conjunction with the accompanying drawings in which.

DETAILED DESCRIPTION OF THE INVENTION

A new apparatus and method for performing operations such as coronary artery bypass grafting surgery on the beating heart operates by tracking a surgical site on the heart surface and by moving a support platform for the tools and/or the hands of the surgeon so that there is substantially no relative motion between them and the surgical area. A series of alternatives for such support are explained in FIGS. 1–13.

Figure 1:
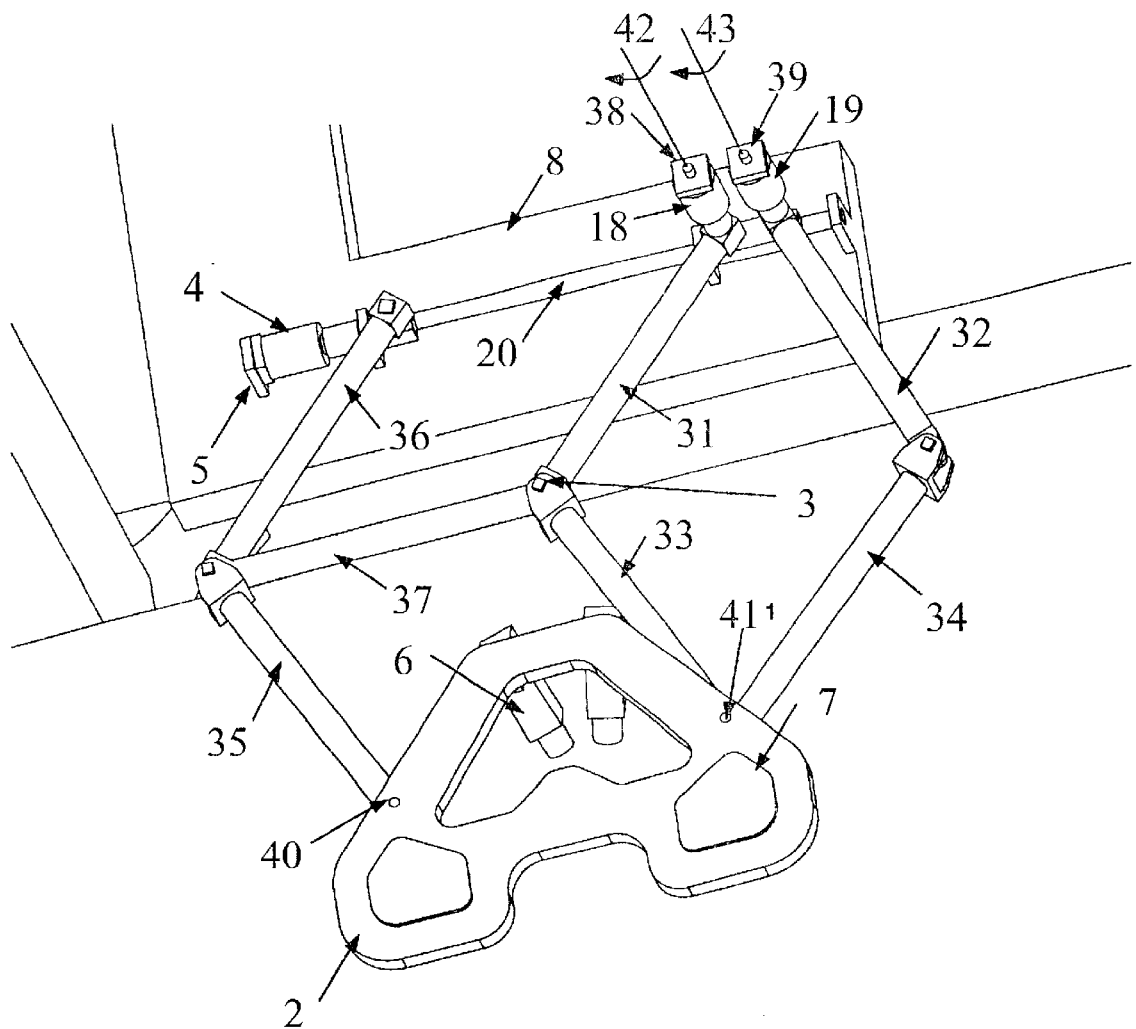
FIG. 1 shows a moving support i.e. platform suitable for use with the present invention.
Figure 2:
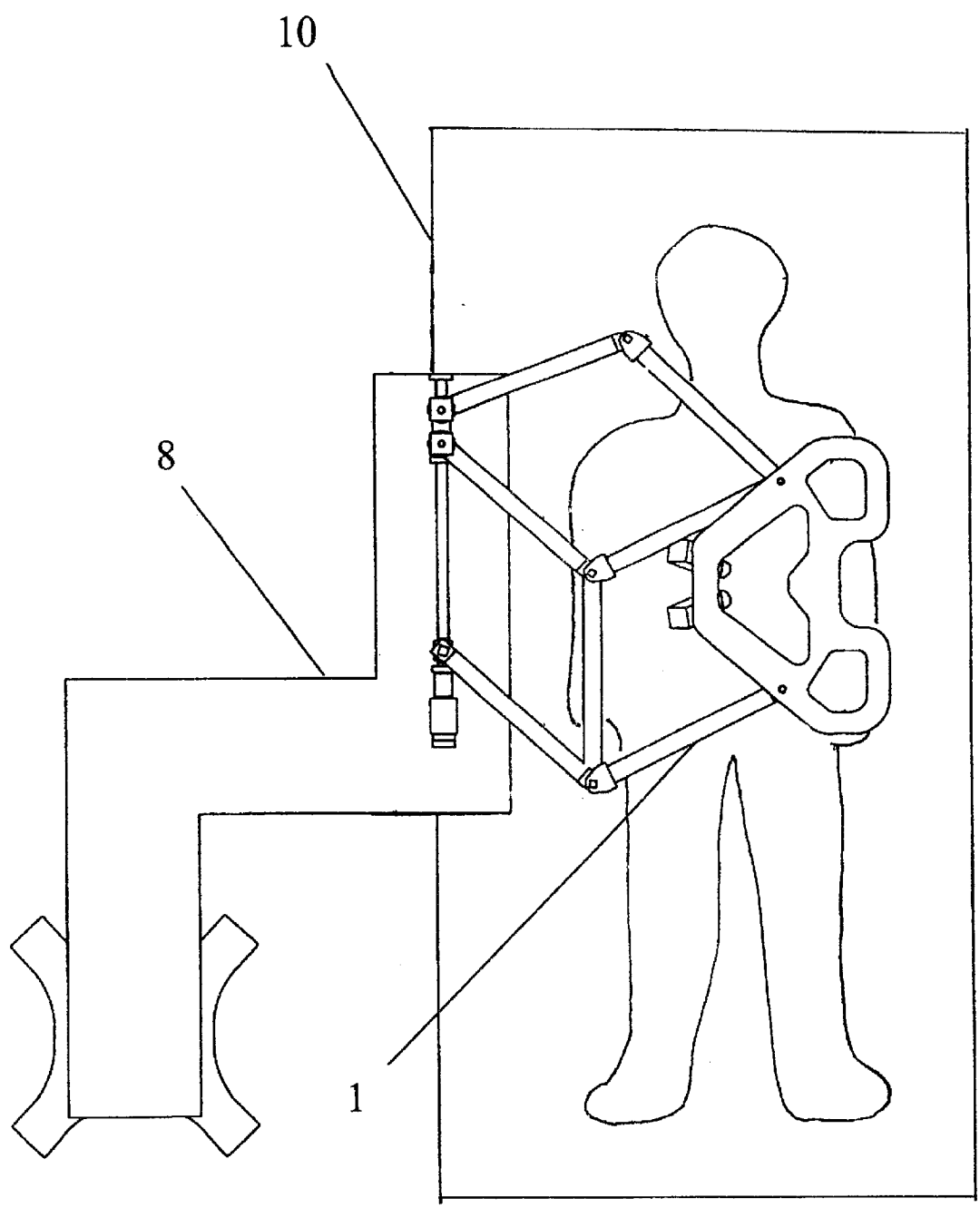
FIG. 2 is a plan view with parts omitted illustrating the mounting of the platform.

FIG. 1 shows a construction of the moving support 1. Support for the hands of the surgeon is provided by an ergonomically designed hand support 7 mounted on a platform 2 mounted on a three-degree of freedom mechanism 3 that determines its motion. The hand support 7 is located on the surface of the platform so that the hands stay in contact with the platform 2 when the suturing is performed.

The mechanism 3 consists of a shaft 20, which can rotate around its axis by means of a motor 4. The shaft 20 is the base link of a 5-bar linkage with links 31, 32, 33 and 34 that move in the same plane. Motor 18 controls the motion of link 31, while motor 19 controls the motion of link 32. Links 20, 31, 37 and 36 form a 4-bar parallelogram linkage, while links 33, 37, 35 and the platform 2 form another parallelogram linkage, such that the attachment points 40, 41 of the platform 2 to the adjacent ends of links 35 and 33 (and 34) define a line parallel to the base motor shaft 20. The mechanism shown in the figure has three degrees of freedom, enough to allow a single point (reference point p discussed below) on or at a fixed displacement relative to the platform 2 to track the motion of a single point s (see FIG. 4) at the surgical site 15 on the heart 12 (see FIG. 3, 7 and 8).

Alternatively, the moving support 1 may provide the platform 2 with up to six degrees of freedom, allowing tracking of a surface patch on the heart and orienting the surgeon's hands accordingly.

Motor shaft angle sensors, e.g. encoders, 5, 38, 39 are attached to the shafts of motors 4, 18 and 19 for control purposes.

A camera or cameras 6 can be attached directly to the platform 2, to provide a steady image of the operating field 12. FIGS. 2,3,4 and 8 schematically illustrate how this method can be used in open heart or minimally invasive direct coronary artery bypass (MIDCAB) surgery.

The moving support 1 is mounted on a base structure 8 that can be placed over the operating site when needed. Although the base structure shown in FIG. 3 is designed to be mounted on the operating room floor 9, it can alternatively be designed so that it can be mounted on the operating table 10.

Figure 3:
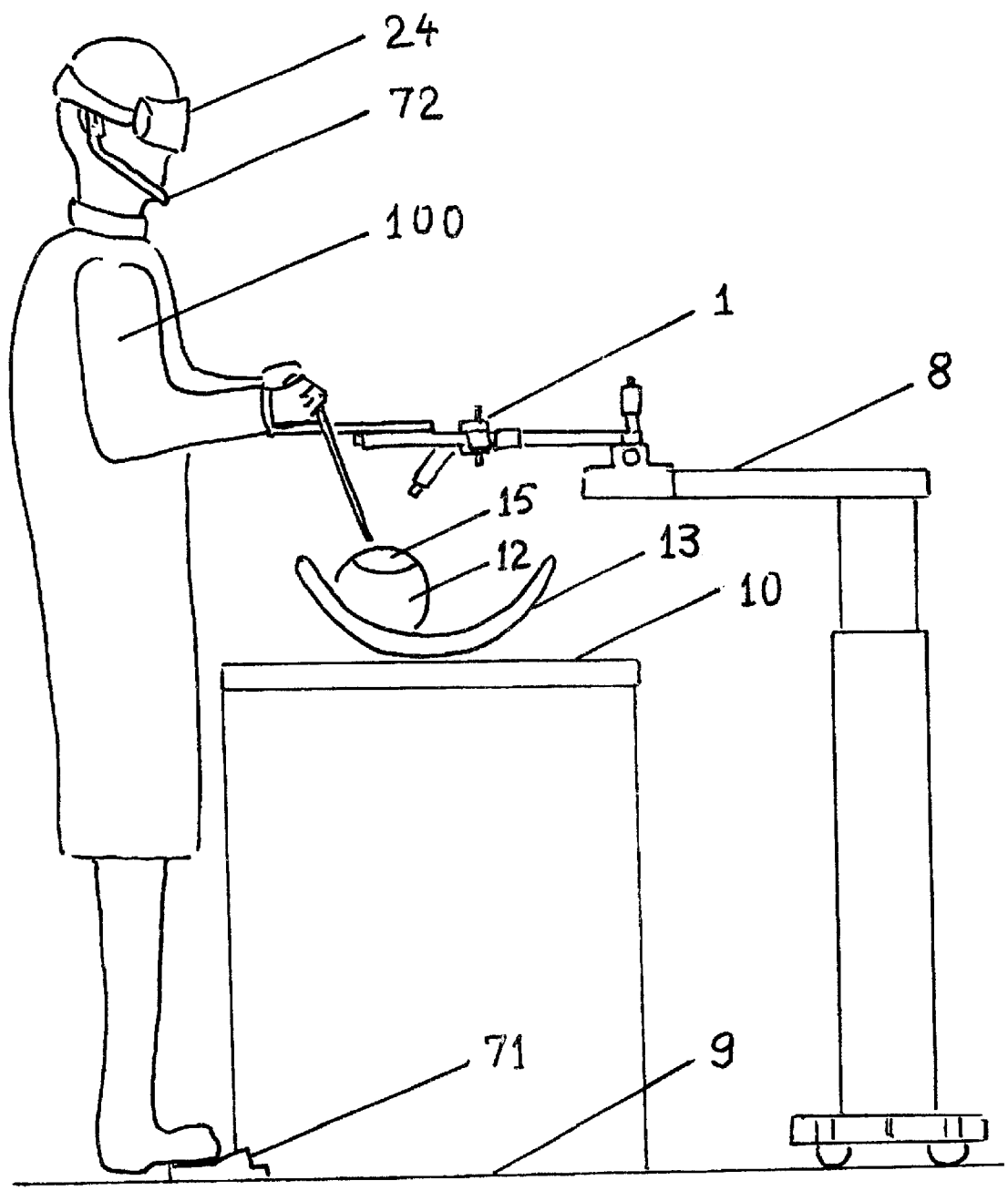
FIG. 3 is an end elevation showing the mounting of the platform with a schematic representation of a heart positioned at the operating site.

FIG. 3 shows the moving support's relative position to the heart schematically indicated at 12 and the patient's body schematically indicated at 13. In addition it shows how the surgeon 100 can place his or her hands on the moving support so that they move in synchrony with the surgical area 15.

A stable image of the surgical workspace can be obtained by attaching, as described above, a camera or cameras 6 to the platform 2 so that they move in synchrony with the surgical area 15. To provide the surgeon 100 with a stereo magnified image the information from the cameras can be displayed for example in a pair of stereo vision goggles or glasses 24, or, alternatively, can be displayed on a high resolution screen viewed with synchronized shutter glasses. Since the cameras are following the surgical area, it is possible to magnify the image as much as necessary and the suturing point will always be in the field of view of the image.

If desired, the camera mounting angle on the motion platform 2 could be made adjustable in order to ease the capture of the surgical area 15 in its field of view. Alternatively, the cameras 6 could be mounted on the motion platform support 8 and the motion of the surgical area 15 could be tracked and stabilized by known image processing techniques.

Figure 13:
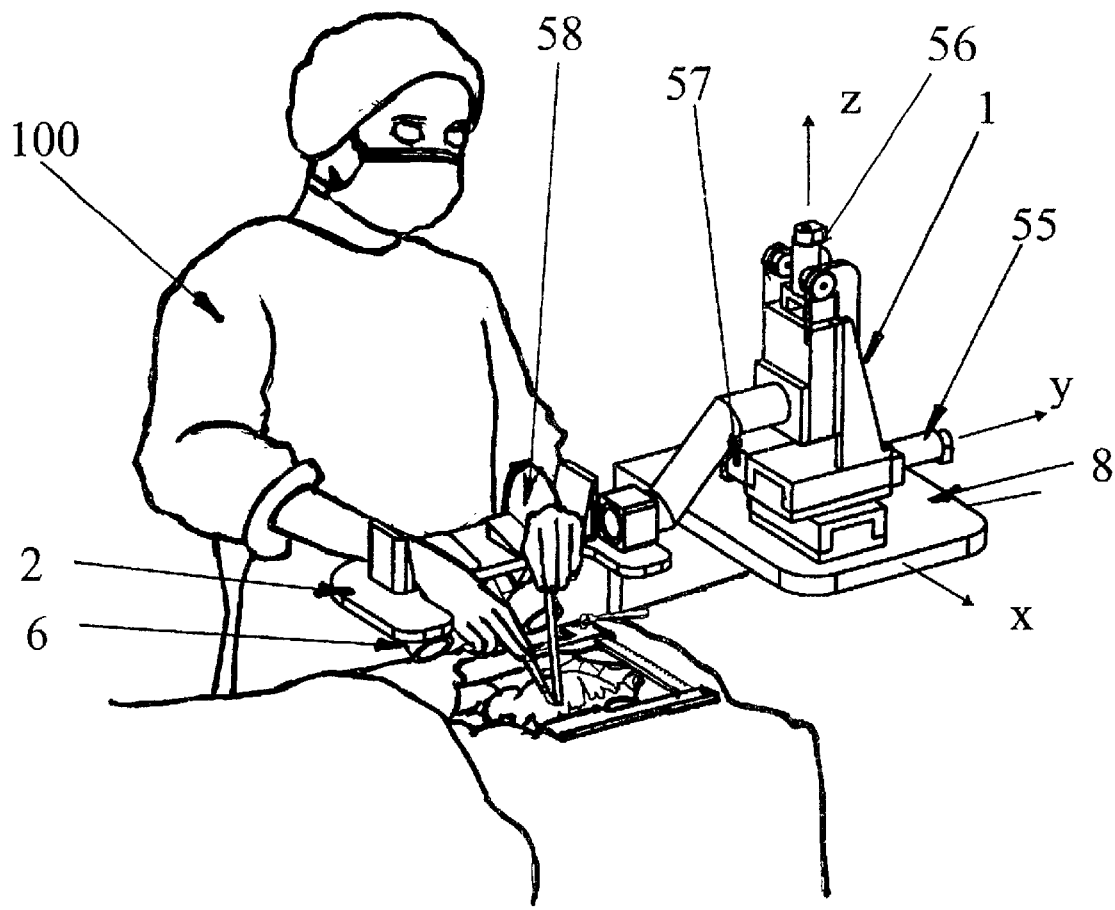
FIG. 13 is an illustration similar to FIG. 3 showing a different mechanical structure for the moving platform.

FIG. 13 shows an alternative construction to the moving platform, using three translational stages with motors, 57 in the x direction, 55 in the y direction and 56 in the z direction, to move the support platform 2. The surgeon's hands are strapped onto the support platform 2 with straps 58. The advantage of such a translational stage construction of the moving platform 2 is that there is no orientation change of the moving platform 2 coupled to the translational change of a single point of the platform 2.

First, a reference (or set) point p, "point p", which is in fixed relationship with respect to the platform 2, is selected. This point could have a default value that is surgeon-dependent, or can be selected by the surgeon at the beginning of the procedure. Likely this point will be close to the tip of the surgeon's instruments when the surgeon's hands are resting on the platform. This point p can be obtained interactively by using, for example, the cameras mounted on the platform 2 to acquire the position of the tip of a hand-held instrument.

The term "point p" is used in the disclosure and claims to define a point or a small volume containing or near the working range of the surgical instruments, fixed in relative position to platform 2 supporting the hands and/or instruments of the surgeon.

Alternatively, a calibration switch 61 (FIG. 4) can be used to select such a point as follows: the surgeon places his hands 62 on the platform and acquires a comfortable position with the instruments 67 in his hands. To find the displacement of the instrument tip 60 relative to the platform 2, the surgeon moves the platform so that the instrument tip 60 (FIG. 4) touches the calibration switch 61. When the calibration switch 61 is tripped, the position of the platform 2 is recorded. Since the position of the switch 61 is known, the position coordinates of the instrument tip point 60 relative to the platform are easily calculated using standard mechanism kinematics. These coordinates define the reference point p fixed to the platform.

Note that the platform can be moved by the surgeon 100 to the calibration switch 61 by using a three-degree-of-freedom joystick 70 that he or she maneuvers with his hand, or by using a three-degree-of-freedom pedal 71 (FIG. 3) or several pedals with fewer degrees of freedom or by using voice commands spoken into a microphone 72 (FIG. 3). Joysticks and pedals with multiple degrees of freedom are easy to construct and use. They generate a constant signal or a signal proportional to the joystick or pedal displacement that can be interpreted by the computer controlling the platform as a velocity signal. The platform motion can be controlled in such a way so as to have the velocity of a known part (for example, the base of the joystick 70) controlled by the joystick displacement.

Alternatively, force sensing may be used to control platform motion. The platform 2 can be provided with a multi-axis force sensor such that when the surgeon 100 pushes or pulls on it, the force is sensed and the computer may be programmed to move the platform in such a way so as to null-out the force. This will allow the surgeon 100 to position the platform 2 by "dragging" it to the desired place.

This reference point p may be easily changed, even during a surgical procedure, in an incremental fashion from the initial point, in a number of ways, for example, by using again a command joystick or force sensor 70, pedals 71 or voice control 72.

Second, the surgeon 100 selects a "point s" on the surface of the heart that he/she wishes to track, i.e., to maintain at fixed displacement relative to the point p in a coordinate frame attached to the platform.

The term "point s" is used in the disclosure and claims to define a reference for the movement of point p (the platform 2) and is intended to include: a specific point on or adjacent to the surgical site 15, an average location of a number of sensed discrete points on or adjacent to the surgical site 15; a volume adjacent to and/or partially containing or containing part of the surgical site 15, or the centroid of such a volume; and/or an object positioned on, or adjacent to the surgical site 15.

Figure 7:
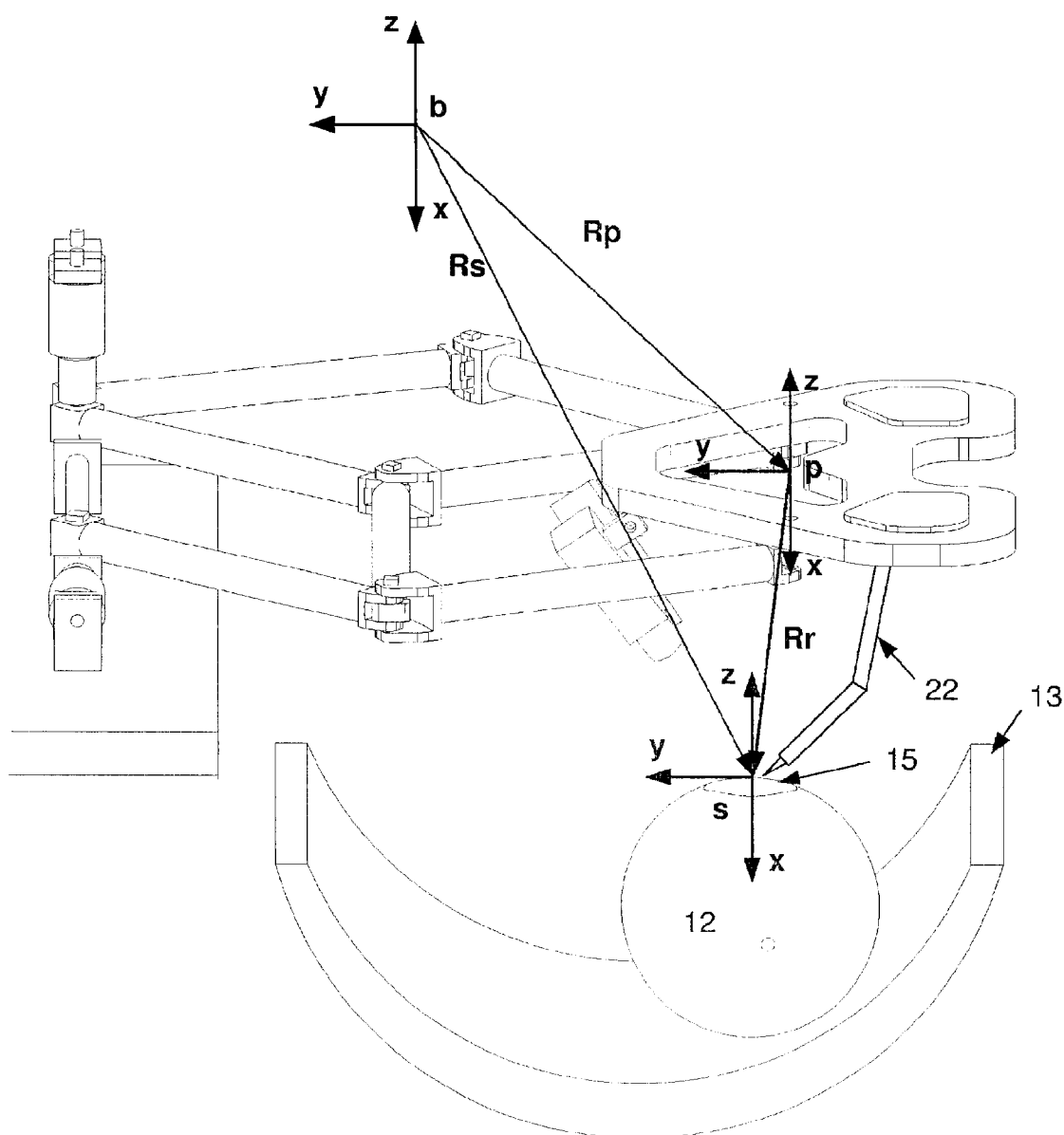
FIG. 7 is an illustration similar to that shown in FIG. 4 but showing a mechanical sensor suitable for the present invention.
Figure 8:
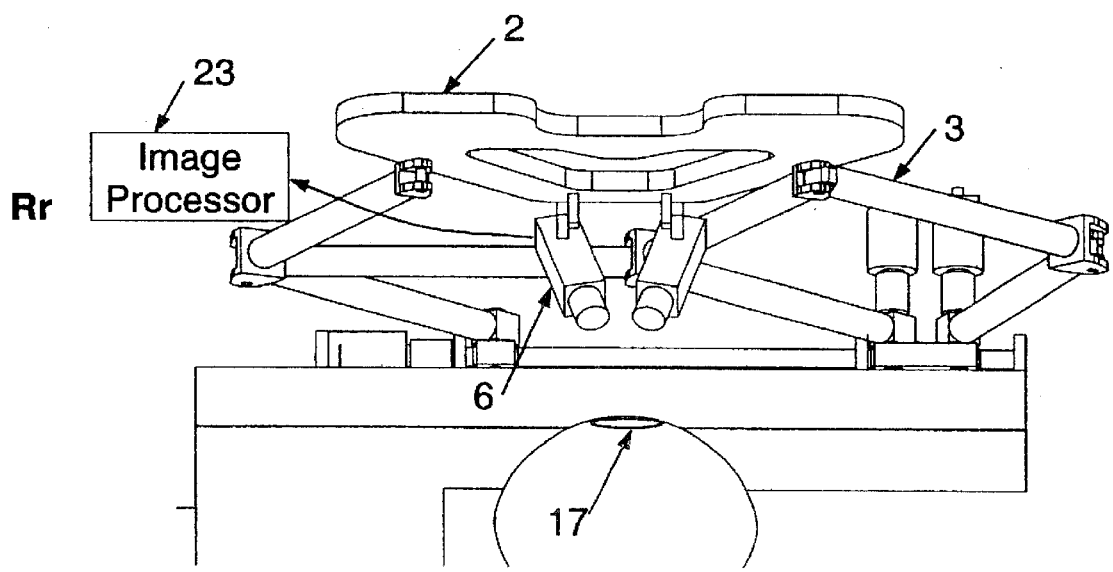
FIG. 8 is an isometric illustration of the platform mounting viewed from below and including an imaging system.

The selection (nature and position) of such a point s depends on the sensor modality employed. For example, if a mechanical sensor 22 as shown in FIG. 7 is used to sense the displacement of the surgical site with respect to the platform, the tip position of the mechanical sensor 22 is known at all times. The surgeon can place the tip of the mechanical sensor 22 onto the (moving) surgical site 15 (point s) and indicate by activating a button, pedal or by voice control when tracking is meant to begin. At that instant, the coordinates of the tip of the mechanical sensor 22 are acquired by the controlling computer and the offset of this tip relative to the moving platform 2 can be easily computed by standard mechanism kinematics.

If an optical sensor based on cameras is used to sense the position of the selected point s, normally on the surgical site, an illuminating pointer can be used to select the point s. For example, a low-power laser pointer 65 (FIG. 4) can be moved by the surgeon under the control of the same joystick 70, voice or pedal 71, to control a narrow beam 64 to illuminate a spot 66 on the heart surface. Obviously to do this the control must be switched from one mode to the other. The optical sensor can acquire the coordinates of such a point s by using, for example, stereo triangulation. As in the case when a mechanical sensor is used, the surgeon can signal the point s to be tracked by activating a button, pedal or by voice command when the illuminated area coincides with his desired selected point s. Third, the surgeon 100 starts the platform tracking when the point of interest s is at a convenient location relative to her hands. The platform then starts moving and keeps the relative displacement Rr between p and s a constant Rd.

Figure 4:
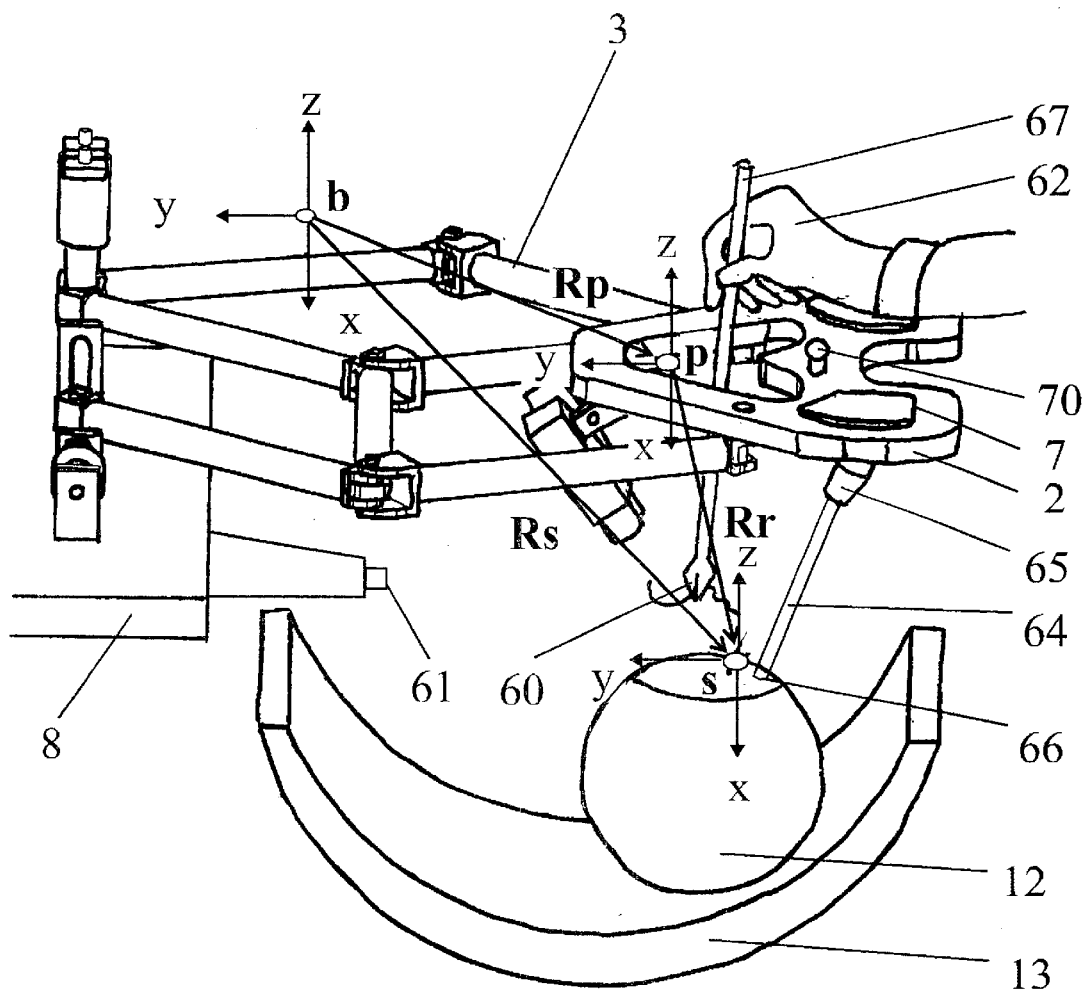
FIG. 4 is an isometric view schematically illustrating the vectors representing movement of the operating site.
Figure 5:
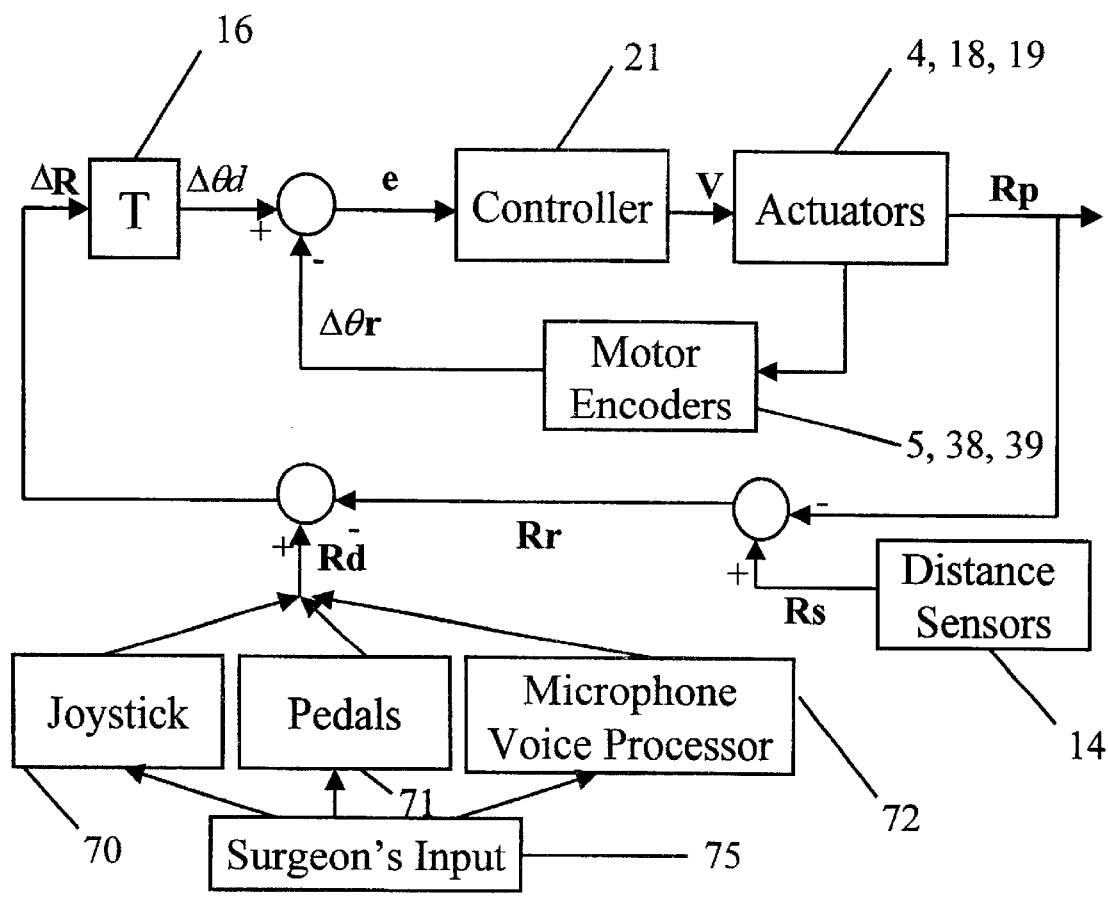
FIG. 5 is a schematic illustration of a sensing and controlling system suitable for the present invention.

FIG. 4 shows the position of the moving support 2 with respect to the surgical area 15, and in conjunction with FIG. 5, shows how the platform can track the heart motion. The reference frame of the platform 2 i.e. point p is displaced by a vector Rp with respect to a base frame b. The reference frame of the surgical area 15 i.e. point s is displaced by a vector Rs with respect to the base frame b. The vector Rr denotes the displacement of the reference frame of the surgical area 15 point s with respect to the reference frame of the platform 2 point p.

Rr=Rs−Rp is shown in FIG. 5, where it is compared to the desired position represented by the constant vector Rd selectable by a surgeon as described below. The vector Rd is defined by the surgeon 100 at the start of the setup, as the desired displacement from the platform 2 point p to the surgical site 15 point s. The difference between these two values is ΔR, which represents the position error in platform coordinates, which is then transformed into actuator coordinates indicated as ΔΓd.

Once the platform and the surgeons' hands are moving with the surgical site, the relative displacement vector Rr can be adjusted by modifying its commanded value Rd by means of a joystick 70, pedals 71 or voice control 72 (see FIG. 5, 6). A large value for Rd means that the point p and the platform 2 is at a large distance from the moving point s. A small value of Rd, for example Rd=[0, 0, 0], means that the points s and p coincide. The joystick 70, the pedals 71 or voice control 72 could be used to make Rd smaller or larger, corresponding to "zooming in" and "zooming out" with respect to the surgical site. Pedals could be used in a simple manner to make the vector Rd and therefore Rr shorter or longer. Voice controls can be used to re-orient, shrink or extend this displacement Rr by issuing commands such as "left", "right", "up", "down", "in" and "out", in a manner similar to the voice control used for controlling the Computer Motion Aesop laparoscopic positioner (see Computer Motion. Automated endoscopic system for optimal positioning, 1998 (http://www.computermotion.com/old/aesop.htm).

Note that the displacement terms Rs, Rp, and Rr are defined in an appropriate manner to match the definitions of "point p" and "point s". If "point p" and "point s" are just points, then Rs, Rp, and Rr are just displacement vectors as expected. If, "point p" and "point s" are sets of points, volumes or objects, Rs and Rp could be defined as centroids of said sets of points, volume or objects, and Rr could be defined as the difference between Rs and Rp or as a displacement vector between sets of points, volumes or objects, according to known geometry concepts, such as, for example, the weighted average between point-to-point distances, or in any other appropriate way that embodies the notion of the selected and set points being close to each other. Usually, the surgical site is small and can be approximated by a single selected point, and its displacement relative to a single selected point on the platform is maintained substantially constant.

Also note that if the support of the motion platform 2 is constructed so it can only translate, not rotate, as shown in FIG. 13, then the separate adjustment of the point p location with respect to the motion platform 2 and of the displacement vector Rd is not necessary, as a change in Rd would exactly correspond to a change in the position of p.

As mentioned previously there are motor axis angle sensors 5, 38, 39 located in the actuators that provide their actual angles as a configuration space vector Δθr. The difference e (error) between the actual Δθr and the desired positions Δθd of the actuators becomes the input to the motor controller 21 which produces the necessary voltage V to adjust the position of the actuators 4, 18, 19 that move the support 1. The motion of the actuators causes the platform 2 to move and to change the distance Rp.

When the motion platform 2 only has translational motion, the transformations from the cartesian space to the actuator space described by Δθr are no longer necessary.

Figure 6:
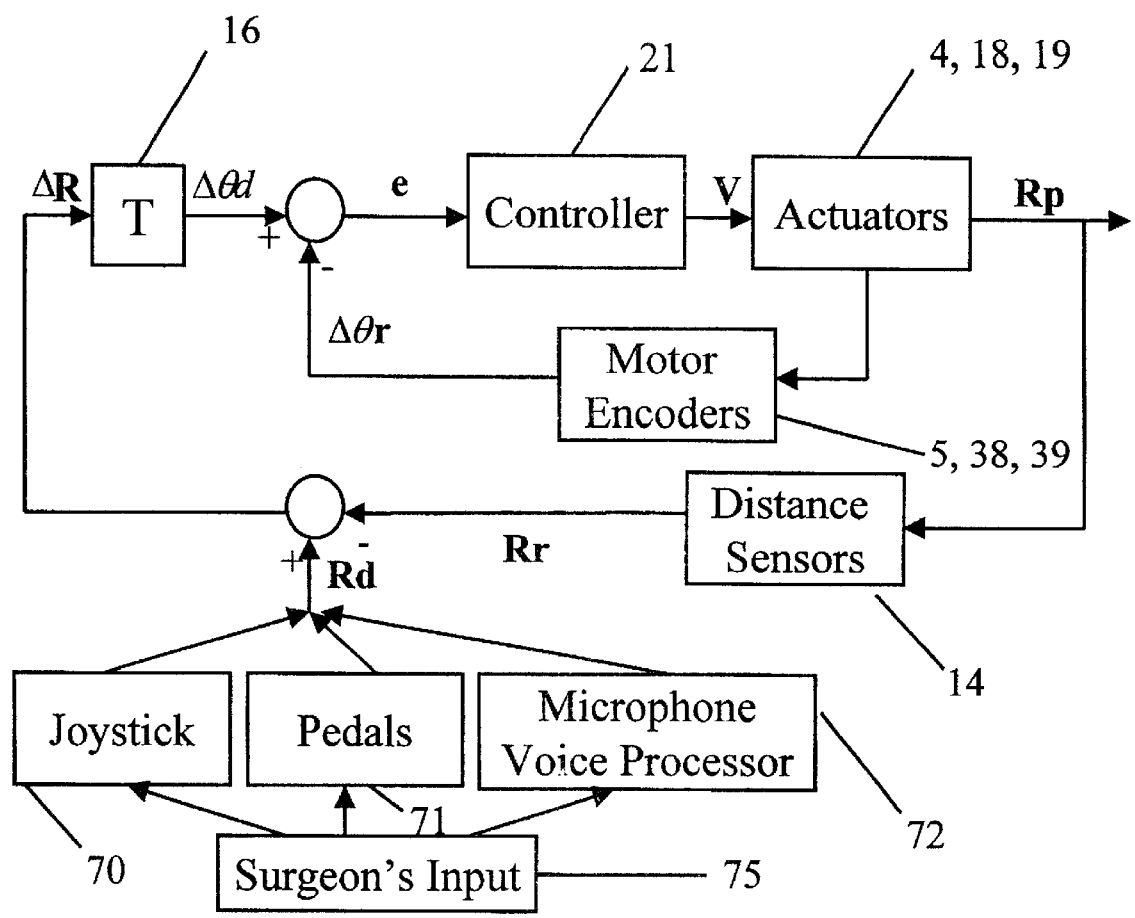
FIG. 6 is a schematic illustration similar to FIG. 5 but showing an alternative sensing and controlling system suitable for the present invention.

Since the heart is in constant motion, it is necessary to determine continuously the displacement Rs from the base frame b to the surgical area point s. This displacement is determined by position sensors as described below. If the sensors are located directly on the platform 2, then the displacement measured is the vector Rr and the control system must be modified as shown in FIG. 6.

One possibility for measuring this displacement consists of placing position or force sensors 22 directly in contact with the heart surface as shown in FIG. 7. The sensor 22 may consist of a light, passive linkage with encoder in its joints, similar, for example, to Immersion Corporation's Microscribe, only much smaller. The encoder values can be read by the control computer that can perform the required kinematic computations to find Rr. This would reduce the complexity of the control process since the platform can follow directly the sensed motion. The sensors shown in the FIG. 7 as being mounted directly on the platform 2 and so they are measuring the vector Rr. However, they can alternatively be mounted on the platform support base 8 or at a different location fixed in the base frame b, to measure a vector Rs.

Figure 9:
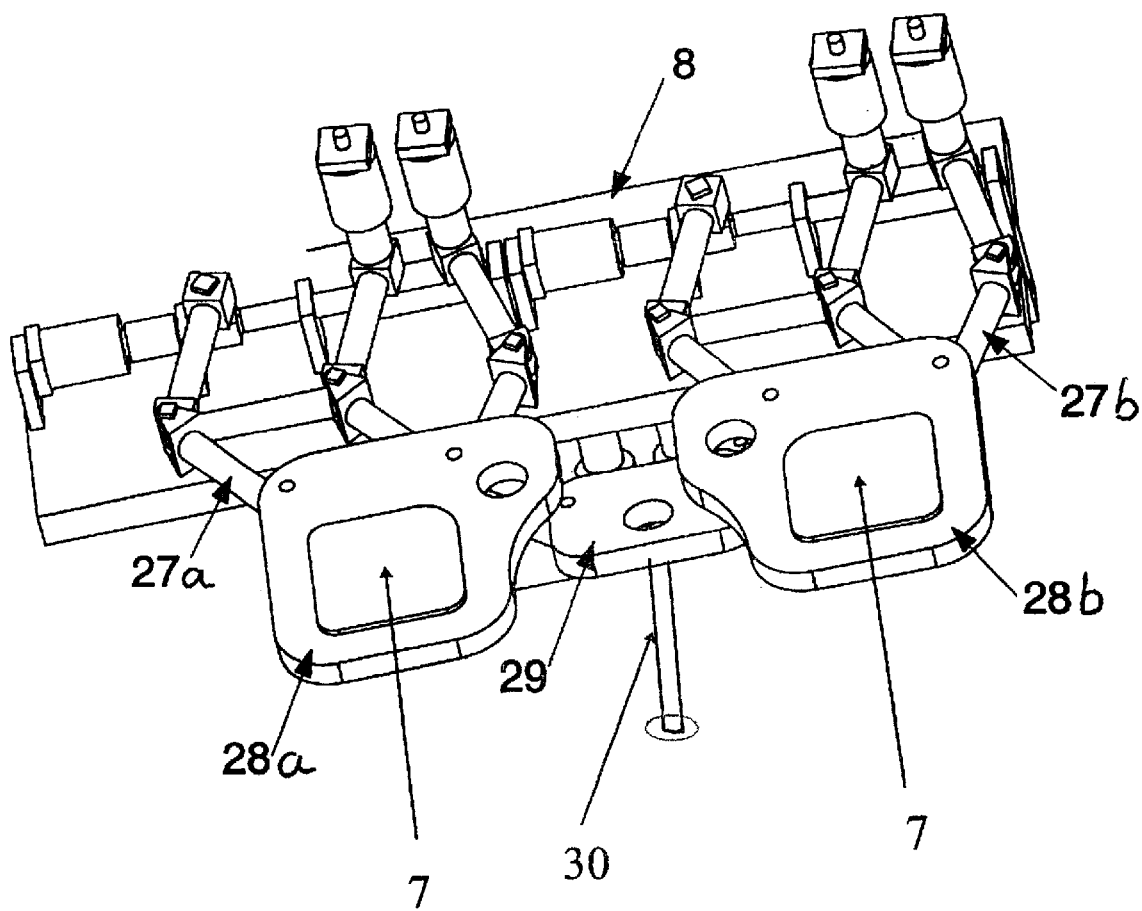
FIG. 9 is an isometric illustration of the platform mounting viewed from above.

Image processing may be used as an alternative to find the displacement vector Rr. This option is more complicated but eliminates the need of direct contact with the heart reducing the risk of damaging the heart tissue. The image from the cameras 6 is analyzed by an image processor 23 to determine the actual distance Rr as shown in FIG. 9. If the cameras were alternatively mounted on a fixed frame the displacement obtained from the image processor 23 would be the vector Rs shown in FIG. 7. To determine the displacement to the surgical site point s by means of image processing it is necessary to focus on a specific point 17 (see FIG. 8) of the surgical area 15 {a feature on the heart surface that can be tracked using known image processing techniques, or, alternatively, a marker on the heart surface at point s at the surgical site 15 could be used for tracking).

Six-degree-of-freedom tracking of small markers using a single camera has been demonstrated before, and so has three-degree-of-freedom motion tracking of image features. In addition to image correlation or other techniques used to detect motion perpendicular to the camera axis, camera focusing can also be used to determine motion parallel to the camera axis. Small fiducial markers can be placed temporarily—attached with small quantities of biocompatible glue, for example.

Alternatively, forces can be measured instead of positions, by using a relatively rigid linkage 22 and a multi-axis force sensor may be mounted between its base and the moving platform 2, or at its tip where the linkage 22 touches the heart. The platform controller is modified to null out the readings of the force sensor, instead of measuring positions, and the distance between the moving platform and the surgical site would be determined by the linkage 22.

The motion of the surgical area on the heart can span an area as large as 2 cm, with a motion frequency that can reach well over 100 beats per minute. Because the coronaries are very small, tracking errors between the sensed point s on the heart and the point p on the platform should be kept very small, preferably to within less than 0.1–0.3 mm.

This is a challenging task that must be accomplished jointly by accurate displacement sensors 14, as well as by the controller 21, both shown schematically in FIG. 5 and 6.

An approach to improve the tracking performance of the platform control is described with reference to FIG. 11.

This approach is based on the fact that heart motion is essentially periodic and that the period of heart motion is the same as the period of the EKG signal and can be detected by standard analog electronics and/or signal processing techniques as described in many references. For example, a heartbeat period detecting circuit can be found in T. Gilhuly, "Optical and Physical Heart Stabilization for Cardiac Surgery," April, 1998. Master's Thesis, Department of Electrical and Computer Engineering, University of British Columbia. If the heart motion were perfectly periodic, the recorded surgical site trajectory or selected point s trajectory over one heartbeat period T from time t−T to time t can be used by the controlling computer to predict the required actuator 4 voltages so that the trajectory of the set point p over the time period t to t+T exactly follows the trajectory of selected point s from time t to time t+T, because this trajectory is the same as the trajectory of selected point s displacement from time t−T to time t. The required actuator 4 voltages can be added to the controller signal that depends on the actual displacement error Rr in FIGS. 5 and 6 and would lead to better controller performance.

In simple terms the rhythm and trajectory(ies) (displacement, velocity and acceleration) of point s of preceding heartbeats are used to set the rhythm and trajectory (ies) of the up-coming movement of point p for the next heartbeat and the movement of point p is corrected based on the current actual or sensed position of point s. Preferred embodiments of this concept are described next.

Figure 10:
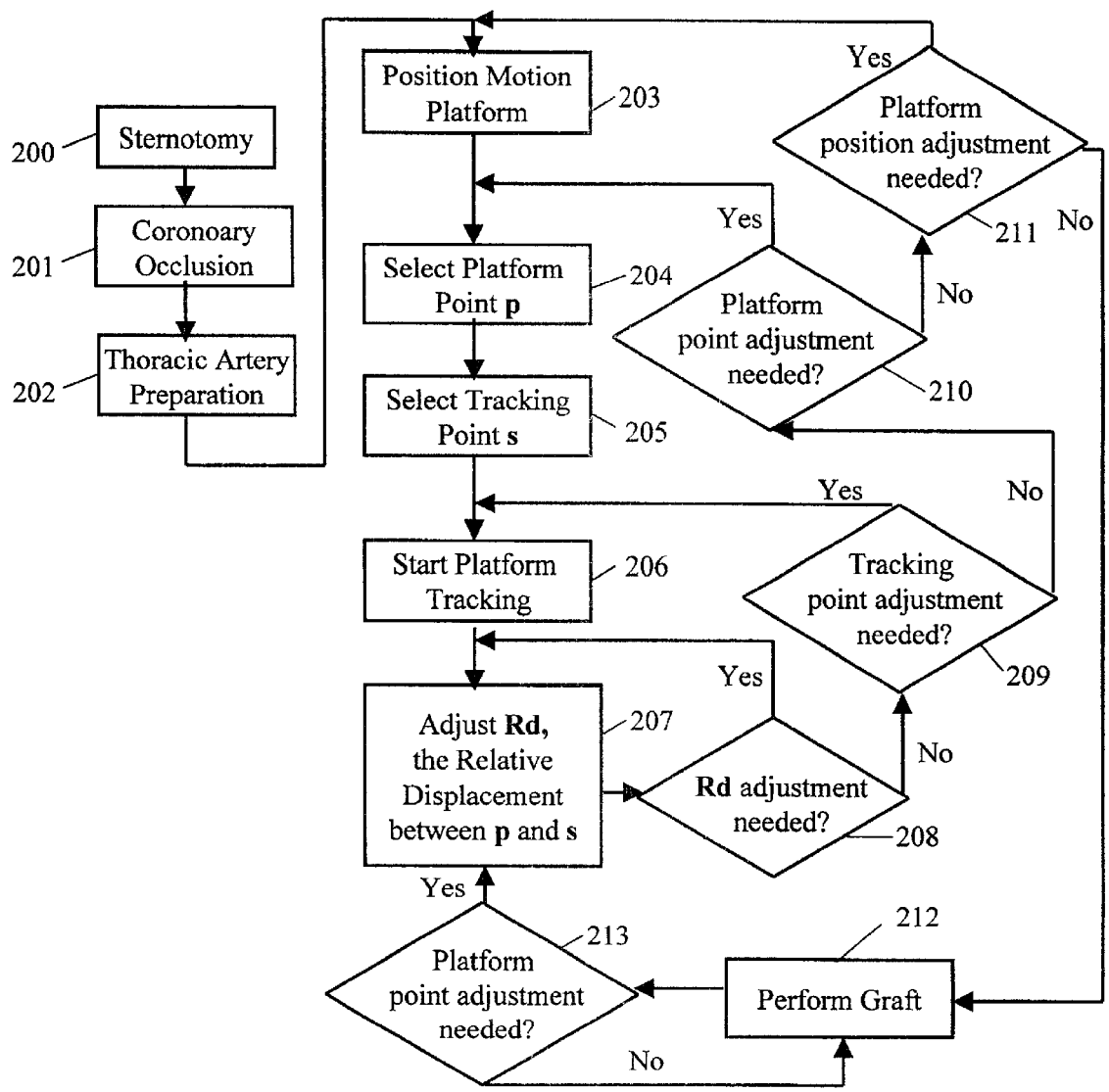
FIG. 10 is a schematic illustration similar to FIGS. 5 and 6 showing a control method using the periodicity of heart movement suitable for the present invention.

If the displacement, velocity and acceleration of the point s on the surgical site could be measured or computed perfectly and with no delay, then it is well known to those skilled in the art (see, for example, F. L. Lewis, C. T. Abdallah, D. M. Dawson, "Control of Robot Manipulators", MacMillan, 1993), that an inverse dynamics procedure could be employed to compute a feedforward or computed torque term Vf (FIG. 11) that could be added to the controller output Vc and that will cause the point p on the moving platform 2 to track the point s on the heart perfectly, i.e., Rp will follow Rs after a short transient caused by initial errors. In general, it is difficult to obtain an accurate feedforward term Vf because velocity and acceleration sensing is expensive, and because electronic or numerical differentiation of the signal Rs in FIGS. 5 and 6 leads to noisy (if low-pass filtering of the signal Rs is not used) or delayed (if low-pass filtering of the signal Rs is used) estimates of the velocity and acceleration of the point s. An approach to computing such a feedforward term Vf is presented that exploits the fact that, under normal circumstances, it is expected that the motion of the heart and consequently the surgical area is quasi-periodic. Thus it is expected that the motion of the surgical site during one heartbeat will closely approximate the motion of the surgical site during the next heartbeat. FIG. 10 shows one embodiment of a feedforward controller that assumes periodicity of the surgical site motion to compute a feedforward term Vf to be added to the controller output Vc that controls the actuators 4. The approach requires an estimate of the heartbeat period and a good model of the motion platform dynamics. In addition, it is useful if the motion platform is not backdriveable by the surgeon's hands so as to have its motion un-influenced by its loading. Basically, the approach involves using the measured position trajectory of the point s over one heart beat to calculate the feedforward actuator input that would produce an identical trajectory of the platform point p, then applying the feedforward actuator input over the next hear beat. If the heart motion is truly periodic, i.e., the change in motion from one heart beat to the next is negligible, the tracking errors between the surgical target point s and the selected platform point p would be also negligible. To accomplish this, first, accurate but phase-delayed estimates of the velocity Vse and acceleration Ase of s are obtained by an estimator 80 (FIG. 11) by known techniques. For example, the velocity Vse could be obtained by filtering Rs by a filter with continuous transfer function $s/[(sT1+1)(sT2+1)]$, where T1 and T2 are small time constants, while the acceleration could be obtained by filtering Rs by a filter with transfer function $[s/(sT1+1)][s/(sT2+1)]$. Rse is just a low-pass filtered version of Rs, for example filtered by $1/[(sT1+1)(sT2+2)]$. Rse, Vse and Ase and a standard inverse dynamics algorithm 81 (FIG. 11) could be used to compute the motor input Ve that would cause Rp to coincide with Rse. This motor torque is then delayed by a block 82 (FIG. 11) by exactly one heartbeat period T minus the phase delay Tp due to the low-pass filtering action in the estimator block 80. The heartbeat period T can be obtained by known EKG processing algorithms embodied in a heartbeat period estimator 83 that takes the heart EKG signal as an input. The output of the delay block 82 is then added to the controller 21 output Vc to generate a platform actuator input V (FIG. 11). Under ideal conditions, the output of the delay block 82 is the platform actuator input that produces a motion platform trajectory such that Rp=Rs. The feedback controller 21 reduces the errors in trajectory tracking due to imperfect model in the inverse dynamics block 81, due to noise and other disturbances. The above embodiment of a feedforward motor torque predictor that uses the periodicity of the heart signal for improved surgical site tracking is just one example. Other techniques can apply in the same spirit. For example, the velocity and acceleration estimator 80 could use a zero-phase digital filter, as described in the Matlab software (Signal Processing Toolbox) as well as in Oppenheim, A. V., and R. W. Schafer, Discrete-Time Signal Processing, Prentice-Hall, 1989, pp. 311–312. Alternatively, zero-phase digital filtering could be used to find the velocity and acceleration estimates of Rs over the last heartbeat period by filtering Rs in the forward direction, then by running the reversed filtered sequences through the filter a second time to cancel any phase delay. The zero-phase digitally filtered velocity and acceleration could be used to compute the feedforward actuator input over the last heartbeat period using an inverse dynamics block. Assuming a periodic heart motion, this feedforward actuator input can be added to the controller 21 output to improve the motion platform trajectory. An accurate knowledge of the delay T and Rs stored over one period are needed for this computation, and T can be obtained again from the EKG signal by using a heartbeat period estimator.

Yet another approach, involving trajectory learning, can be used to improve the controller tracking performance by using the periodicity of heart motion. For example, a trajectory learning approach is described in C. H. An, C. G. Atkeson and J. M. Hollerbach, "Model-Based Control of a Robot Manipulator", MIT Press, Cambridge, Mass., 1988, that teaches how the actuator controls can be improved for repetitive motions. The method involves the use of a correction signal to the actuators 4 over one period of the motion in order to decrease the trajectory error between the points p and s sensed over the previous period of the motion. What is required for application of the method is a model of the motion platform dynamics and an accurate estimate of the heartbeat period. In the case of open-heart surgery, with the use of the proposed method, surgery would likely proceed in the manner described in John L. Ochsner and Noel L. Mills. Coronary Artery Surgery. Henry Kimpton Publishers, London, 1978 and/or Bradley J. Harlan, Albert Starr, and Frederic M. Harwin, Manual of Cardiac Surgery, Springer-Verlag, Berlin, 1980.

Almost all primary and secondary cardiac procedures are performed through a median sternotomy. A skin incision is made in the midline from below the sternal notch to the line alba below the xiphoid process. The sternum is divided longitudinally and the sternal periosteum is electrocoagulated. Once the thoracic cavity is accessible, a sternal retractor 11 is inserted and opened to expose the heart 12.

Following sternotomy incision, one side of the sternum is elevated in order to expose the undersurface of the chest wall. The internal thoracic artery (ITA) is dissected using electrocautery. To be able to perform a graft without the use of the cardiopulmonary bypass, it is necessary to obtain a dry operative field. This can be obtained by isolating a particular segment of the heart from its blood supply, also called coronary occlusion. Once the coronary occlusion is performed the internal thoracic artery is prepared for the graft or grafts. The moving support is placed on top of the patient. It should be placed as close as necessary to perform all the grafts taking into account that the distance Rd (from the point p on the platform 2 to the point s in the surgical area 15) will remain constant throughout the suturing procedure.

Once it is in the desired position, the distance sensors 14 start measuring the motion of the heart and the support starts moving. When the motion is stabilized and the platform is moving in synchrony with the surgical area, the graft is performed. The artery is grafted to the coronary artery with a continuous stitch for two-thirds the length of the arteriotomy on one side. The opposite side is sutured in a similar manner. Five to seven interrupted stitches are used to complete the anastomosis, at which point the moving support can be moved aside and coronary occlusion can be removed.

Figure 11:
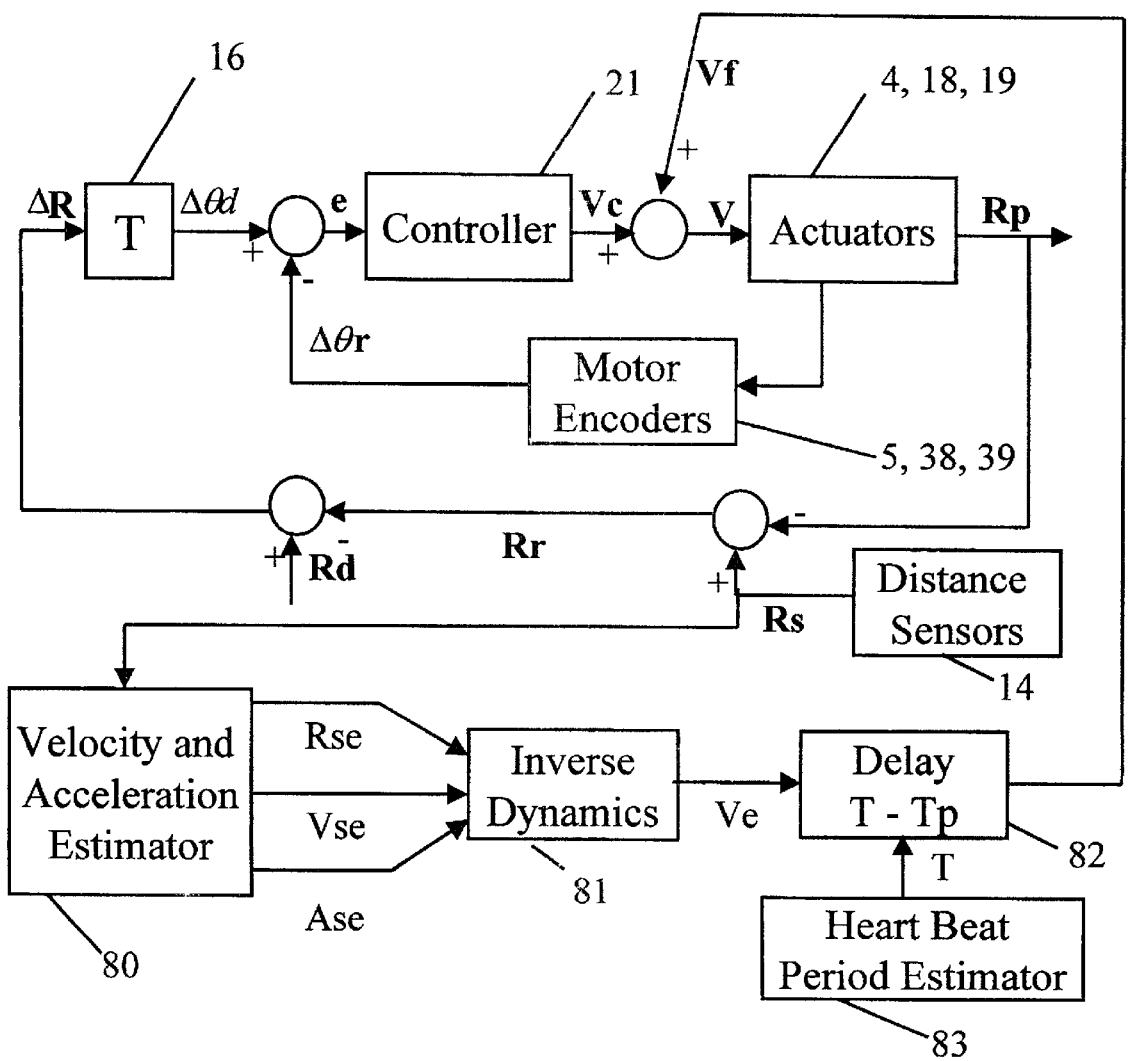
FIG. 11 is a flow diagram illustrating a procedure a surgeon may follow in using the proposed motion-tracking platform.

A preferred method for setting up the tracking system for surgery on the beating heart is summarized in the flow diagram showed in FIG. 11. First, (200) a sternotomy is performed to expose the heart, followed by (201) coronary occlusion and preparation of the thoracic artery for grafts (202). Then, (203) the moving support is placed above the patient. A point p on the motion platform is selected as according to the procedure outlined above (204). A second point s is selected (205) on or near the surgical site according to the procedure outlined above. The platform tracking is put in motion (206), once the controlling computer confirms successful tracking of the point s. If needed (208), the relative displacement Rd between points s and p is adjusted (207) using joystick, pedal, voice or other type of control. If needed (209), the surgeon can re-acquire the tracking point. If needed (210), the surgeon could adjust the platform point p by joystick, pedal, voice or other type of control, as described before. If needed (211), the placement of the motion platform apparatus can be adjusted relative to the patient/operating table by the surgeon and surgical staff. Obviously, a mode switching between the control of p, Rd and acquisition of the point s to be tracked can be accomplished by another pedal, a voice command, or additional mode-switching switches. The graft is then performed (212) on the beating heart. Should tracking control deteriorate because of disturbances, noise or erratic heartbeats, a decision to re-adjust the tracking could be made (213).

Thoracoscopic Surgery

Figure 12:
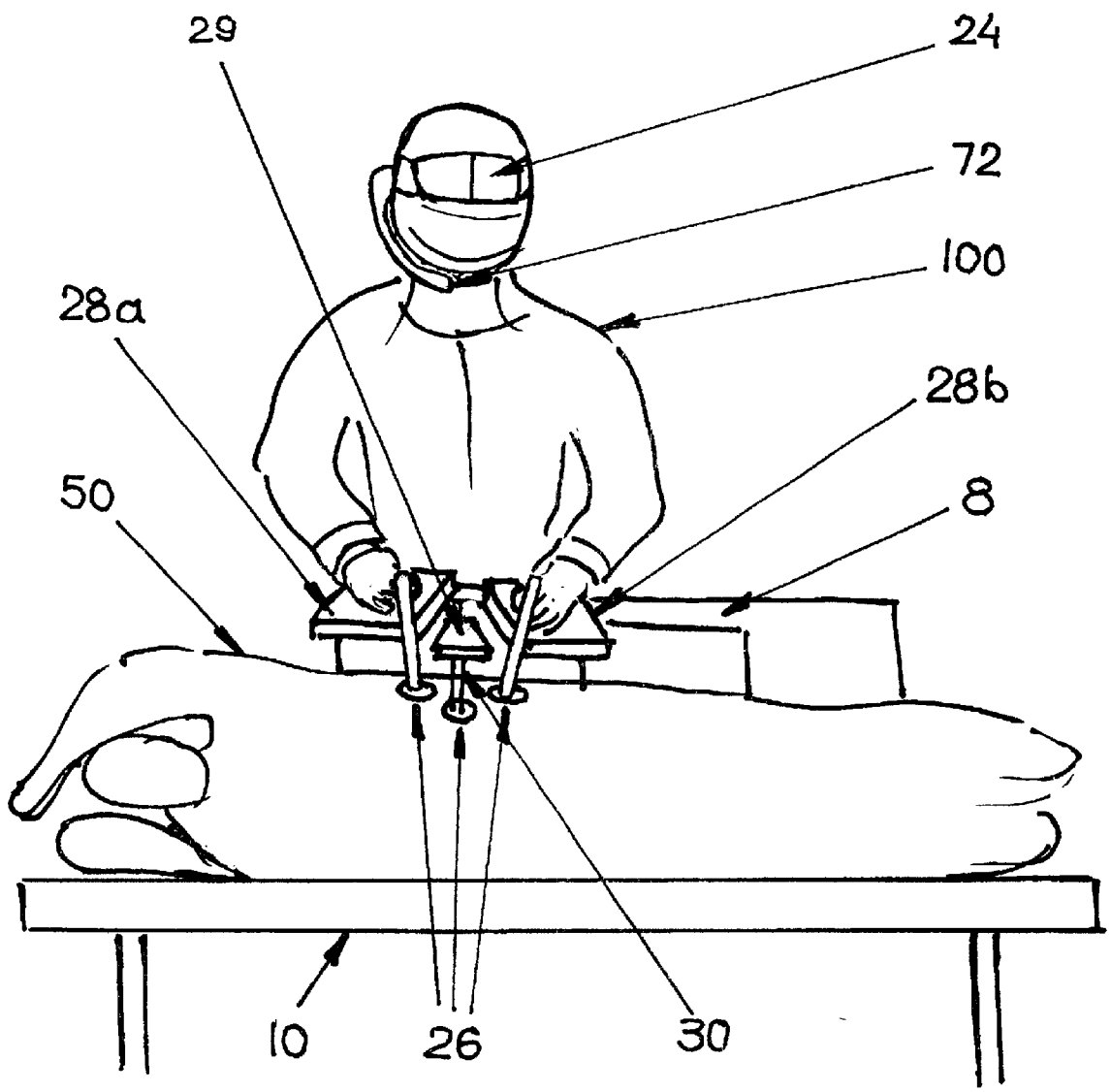
FIG. 12 is an illustration showing a motion platform suitable for thoracoscopic surgery on the beating heart.

FIG. 9 and FIG. 12 show a possible construction of a moving support for Thoracoscopic surgery. The patient 50 is shown on the operating bed 10, with the surgeon 100 operating through chest ports 26 on a beating heart with the aid of two moving platforms 28a and b that track the motion of the surgical site. Since the tools 25 are inserted through separate small incisions 26, their distal end motion may not be the same, because the two different portal constraints may amplify the motion necessary to have the tip of the two instruments follow the same selected point s on the surgical site. It is therefore necessary to have two different mechanisms 27 (a and b) and platforms 28 (a,b) for each of them. It is also necessary to have an additional moving support 29 for the endoscope 30 in order to view the surgical site. An alternative to moving the camera would be to use image processing to follow a point on the heart surface to obtain a stable image of the workspace. This can be done with known image processing techniques as used in image stabilization. Support for the hands 7 is provided so that there is more control of the tools. The motion of the moving support is controlled as explained earlier. The procedure for thoracoscopic surgery is as follows.

The patient 50 is placed at a 30 degree angle to the right with the left arm elevated above the head or in the normal position. Three lateral chest ports 26 are made between the fourth, fifth and sixth intercostal spaces. The left lung is deflated to provide a better access to the operative field. A thorascope is placed through one of the incisions. While the surgeon manipulates the tools, the assistant can guide the endoscope supported by platform 29 so that it focuses on the surgical site. An alternative to this approach would be to use a robotic arm to guide the endoscope, such as the Aesop system from Computer Motion. The internal thoracic artery (ITA) is then dissected, clipping all branches and preparing the incision for the anastomosis. With the aid of the hand and tool support, the graft to the coronary artery is performed following a procedure as described earlier for a single hand support, both in terms of apparatus and method.

Throughout the disclosure reference is made to the heart and to heart surgery, however the present invention may also be applied to other suitable applications The disclosure has dealt with the use of a single selected point s on the heart or other organ or area to be operated on and controls the position of a single set point p fixed in position relative to the platform. It will be apparent that a number of selected points s could be monitored and for example averaged to provide a control signal maintaining the point p with the desired fixed displacement relative to the operating site as represented by the point s. Also the disclosure has dealt with a single point p fixed relative to the platform, it will be apparent that if the mounting for the platform has sufficient degrees of freedom (i.e. more than 3 and generally 6 degrees of freedom) more than one point p may be set in fixed relationship to the platform and the position of each such point p independently controlled by its respective selected point s. Such multiple controls may be used, for example, to change the angle or orientation of the platform to maintain it at the same orientation as the surgical site.

Having described the invention modifications will be evident to those skilled in the art without departing from the spirit of the invention as defined in the appended claims

We claim:

1. A method for performing surgery comprising sensing the movement of a selected point s at or adjacent to a surgical site in a plurality of different directions and controlling the movement of a defined set point p having a location fixed relative to a platform said platform having at least three degrees of freedom of movement, by controlling movement of said platform in said at least three degrees of freedom in accordance with said sensed movement so as to maintain a set displacement between said selected point s and said set point p substantially constant.

2. A method as defined in claim 1 wherein said set displacement between said selected point s and said set point p is selectively defined.

3. A method as defined in claim 2 wherein said selectively defining comprises controlling by a voice control.

4. A method as defined in claim 2 wherein said selectively defining comprises controlling by a joystick control.

5. A method as defined in claim 2 wherein, said selectively defining comprises controlling a foot pedal.

6. A method as defined in claim 2 wherein said method further comprises selecting said set point p, selecting said selected point s and selecting the desired position of said set point p relative to said selected point and then commencing said controlling the movement of said set point p.

7. A method as defined in claim 1 wherein said surgical site is on a heart and wherein said controlling comprises determining trajectory of point s based on previously sensed historical movement of point s and rhythm of said point s and wherein said controlling controls said movement of said platform and thereby movement of said point p based on said historical movement of point s and correcting said movement of point p based on current sensed movement of point s.

8. A method as defined in claim 2 wherein said surgical site is on a heart and wherein said controlling comprises determining trajectory of point s based on previously sensed historical movement of point s and rhythm of said point s and wherein said controlling controls said movement of said platform and thereby movement of said point p based on said historical movement of point s and correcting said movement of point p based on current sensed movement of point s.

9. A method as defined in claim 6 wherein said surgical site is on a heart and wherein said controlling comprises determining trajectory of point s based on previously sensed historical movement of point s and rhythm of said point s and wherein said controlling controls said movement of said platform and thereby movement of said point p based on said historical movement of point s and correcting said movement of point p based on current sensed movement of point s.

10. A method as defined in claim 1 wherein said surgical site is on a heart and wherein said controlling comprises means for determining the period T of the motion of said surgical site, means for computing a predictive part of the control signal based on historical movement of point s, and a platform controller generating a control signal comprising said predictive part delayed by approximately T seconds and a feedback part dependent on current sensed movement of point s.

11. An apparatus for assisting a surgeon in performing surgery comprising a sensor for sensing the movement in a plurality of directions of a selected point s at or adjacent to a surgical site, a computer, means for providing said sensed movement to said computer, a surgical platform, a set point p fixed in position relative to said platform, means for mounting said platform for movement permitting at least three degrees of freedom of movement, said computer controlling movement of said platform and thereby set point p in said movement along said three degrees freedom in accordance with said sensed movement of said selected point s to maintain a set displacement between said set point s and said selected point p substantially constant.

12. An apparatus as defined in claim 11 further comprising means to selectively define said set displacement between said selected point s and said set point p.

13. An apparatus as defined in claim 12 wherein said means to selectively define comprises a voice control.

14. An apparatus as defined in claim 12 wherein said means to selectively define comprises a joystick control.

15. An apparatus as defined in claim 12 wherein, said means to selectively define comprises a foot pedal control.

16. An apparatus as defined in claim 11 wherein said surgical site is on a heart and wherein said computer is programmed to determine rhythm and trajectory of point s based on previously sensed historical movement of point s and to control movement of point p based on said historical movement of point s and correcting said movement of point p based on current sensed movement of point s.

17. An apparatus as defined in claim 12 wherein said surgical site is on a heart and wherein said computer is programmed to determine rhythm and trajectory of point s based on previously sensed historical movement of point s and to control movement of point p based on said historical movement of point s and correcting said movement of point p based on current sensed movement of point s.

18. An apparatus as defined in claim 12 further comprising camera system mounted in fixed relationship with said platform to provide a stabilized view of said surgical site.

19. An apparatus as defined in claim 12 further comprising camera system mounted in fixed relationship with said platform to provide a stabilized view of said surgical site.

* * * * *